United States Patent [19]

Miller et al.

[11] Patent Number: 5,707,394

[45] Date of Patent: Jan. 13, 1998

[54] PRE-LOADED SUTURE ANCHOR WITH RIGID EXTENSION

[75] Inventors: Peter C. Miller, Largo; Joseph Fucci, Palm Harbor, both of Fla.

[73] Assignee: Bristol-Myers Squibb Company, New York, N.Y.

[21] Appl. No.: 704,480

[22] Filed: Aug. 22, 1996

Related U.S. Application Data

[63] Continuation-in-part of Ser. No. 597,792, Feb. 7, 1996.

[51] Int. Cl.$^6$ .................................................. A61B 17/04
[52] U.S. Cl. ........................... 606/232; 606/148; 606/130
[58] Field of Search ............................ 606/232, 145, 606/148, 75, 73, 104, 139

[56] References Cited

U.S. PATENT DOCUMENTS

| | | |
|---|---|---|
| 4,244,370 | 1/1981 | Furlow et al. . |
| 4,409,974 | 10/1983 | Freedland . |
| 4,631,100 | 12/1986 | Somers et al. . |
| 4,738,255 | 4/1988 | Goble et al. . |
| 4,741,330 | 5/1988 | Hayhurst . |
| 4,898,156 | 2/1990 | Gatturna et al. . |
| 4,968,315 | 11/1990 | Gatturna . |
| 4,976,712 | 12/1990 | Vandersilk . |
| 4,989,764 | 2/1991 | Hoffman et al. . |
| 5,034,012 | 7/1991 | Frigg . |
| 5,037,422 | 8/1991 | Hayhurst et al. . |
| 5,041,129 | 8/1991 | Hayhurst et al. . |
| 5,084,063 | 1/1992 | Korthoff . |
| 5,100,417 | 3/1992 | Cerier et al. . |
| 5,102,421 | 4/1992 | Anspach, Jr. . |
| 5,139,520 | 8/1992 | Rosenberg . |
| 5,141,520 | 8/1992 | Goble et al. . |
| 5,156,616 | 10/1992 | Meadows et al. . |
| 5,176,682 | 1/1993 | Chow . |
| 5,224,946 | 7/1993 | Hayhurst et al. . |
| 5,258,016 | 11/1993 | Dipoto et al. . |
| 5,268,001 | 12/1993 | Nicholson et al. . |
| 5,368,595 | 11/1994 | Lewis . |
| 5,534,011 | 7/1996 | Greene, Jr. et al. . |
| 5,578,057 | 11/1996 | Wenstrom, Jr. ......................... 606/232 |

OTHER PUBLICATIONS

Article entitled "Mini–Statak Soft Tissue Attachment Device", Fracture Management, Zimmer, Feb. 1992, 4 pages.
Article Entitled "Statak Soft Tissue Attachment Device", Fracture Management, Zimmer, Rev. Nov. 1989, 4 pages.
Product Information, "Rotator Cuff Repair with a New Twist" Linvatec, 1993, 2 pages.

*Primary Examiner*—Michael Buiz
*Assistant Examiner*—Tina T. D. Pham
*Attorney, Agent, or Firm*—Gene Warzecha

[57] ABSTRACT

A method and apparatus for facilitating use of a threaded suture anchor in combination with a reusable cannulated anchor driver. The device enables a suture anchor to be preassembled with a suture so that a user need not assemble a suture anchor with suture immediately prior to use. The preassembled anchor/suture is provided with a suture stiffening or support means by which the free ends of the suture may be easily threaded into the axial bore of a cannulated driver. The stiffening means may comprise an elongated rod abuttingly joined to the free ends of suture (threaded through a suture anchor) and secured thereto by a length of shrinkable tubing frictionally engaging the free ends of the suture and one end of the rod.

8 Claims, 4 Drawing Sheets

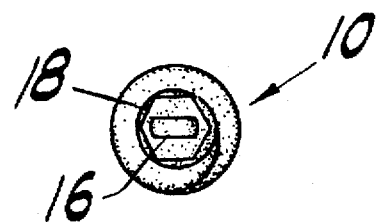
Fig. 3
Prior Art
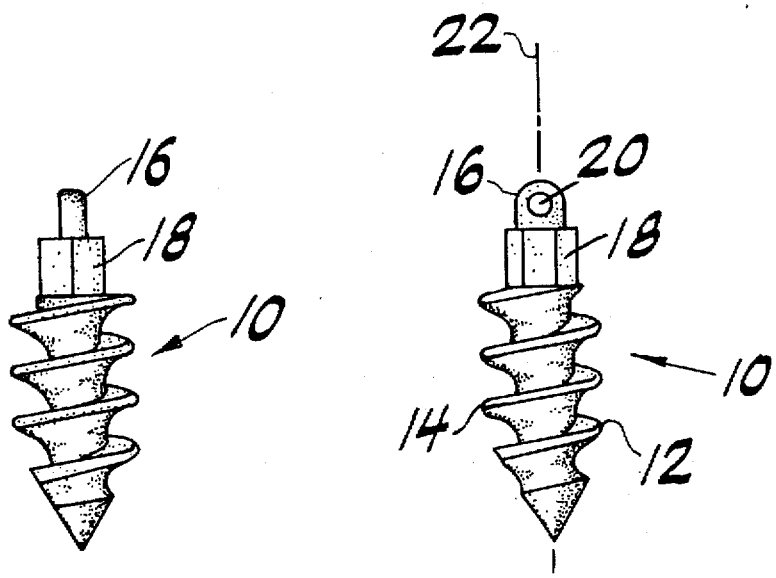
Fig. 2
Prior Art
Fig. 1
Prior Art

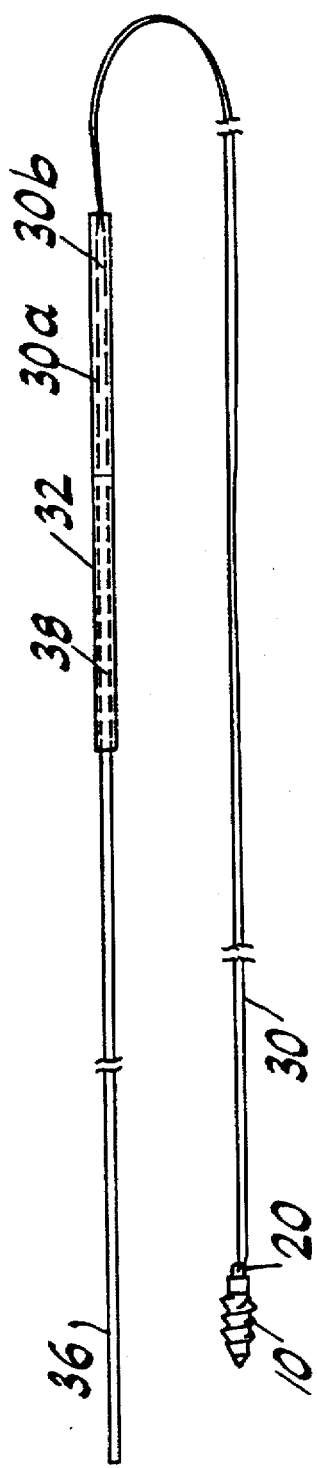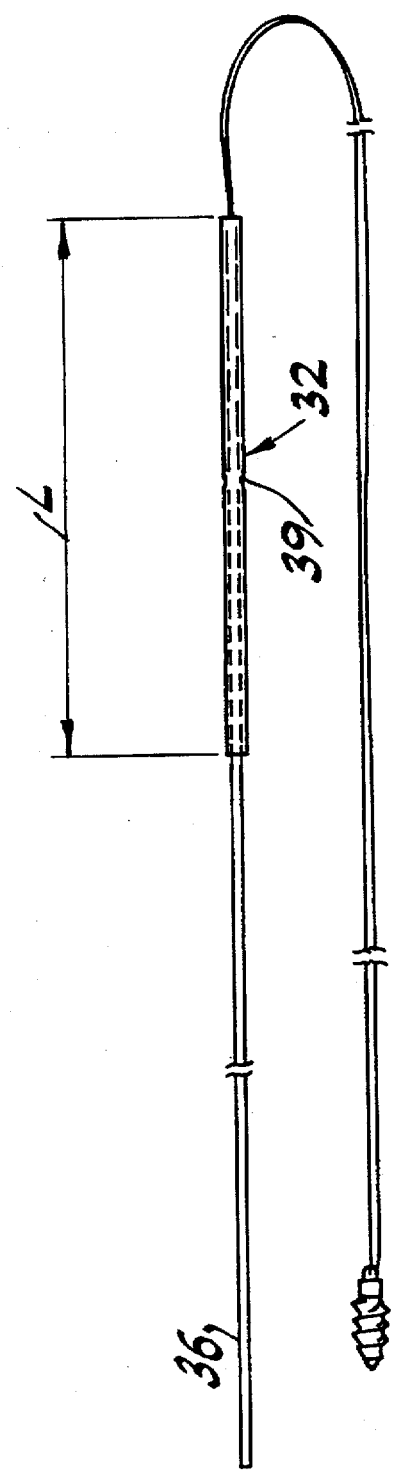
Fig. 4a
Fig. 4b

PRE-LOADED SUTURE ANCHOR WITH RIGID EXTENSION

This application is a continuation-in-part of pending application Ser. No. 08/597,792, filed Feb. 7, 1996.

BACKGROUND OF THE INVENTION

1. Field of the Invention

The invention relates generally to suture anchors for attaching soft tissue to bone. More particularly, the invention relates to a method and apparatus for producing a pre-loaded suture anchor assembly to facilitate attachment of a threaded suture anchor to a cannulated suture anchor driver for attaching the suture anchor at a selected work site.

2. Description of the Prior Art

In the course of certain surgical procedures, soft tissue is secured to a selected bone surface either directly, via some type of implant, or indirectly via an implant (i.e. an anchor) to which suture is attached, the suture then being tied to the soft tissue to hold it in place. Anchors may be used to attach soft tissue such as ligaments, tendons, muscles, etc. to a surface from which the soft tissue has become detached and may also be used to secure soft tissue to supplementary attachment sites for reinforcement. For example, in urological applications anchors may be used in bladder neck suspensions to attach a portion of the bladder to an adjacent bone surface. Such soft tissue attachment may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body.

The prior art includes numerous types of suture anchors adapted to be secured in the bone, sometimes directly in one step and sometimes in pre-drilled holes or tunnels. The term "suture anchor" is used broadly and will be understood to refer to devices having a similar structure even if material other than suture is connected to the device. These devices generally comprise an anchor body designed to be embedded in the bone at a selected work site and a length of suture or other elongated structure extending from the body. The suture provides a means to tie the soft tissue adjacent the bone into which the anchor body has been embedded. While suture is sometimes tied to a portion of the anchor body, often the suture is threaded (i.e. pre-loaded) through an eyelet or other aperture in the anchor body so the suture may slide within the eyelet to facilitate subsequent knot tying steps. Alternatively, the suture may be non-slidably attached to have one or two fixed-length ends extending from the anchor body. Some prior art suture anchors are elongated and have annular ribs or radially extending barbs and are required to be pushed or hammered directly into bone or into a pre-formed bone tunnel (exemplified by U.S. Pat. No. 5,102,421 (Anspach, Jr.); U.S. Pat. No. 5,141,520 (Goble et al.); U.S. Pat. No. 5,100,417 (Cerier et al.); U.S. Pat. No. 5,224,946 (Hayhurst et al.) and U.S. Pat. No. 5,261,914 (Warren)). Other suture anchors are threaded in order to be screwed into bone as exemplified by U.S. Pat. No. 5,156,616 (Meadows et al.) and U.S. Pat. No. 4,632,100 (Somers et al.).

Devices used to insert suture anchors into bone surfaces are known as drivers and provide an interface between the actual implant and the surgeon performing the procedure. While this interface is most important in endoscopic surgical procedures because of the limited accessibility of the surgical site, prior art endoscopic procedures generally utilize devices and methods designed for open surgical procedures. All known procedures used to insert suture anchors endoscopically rely on elongated extensions which pass through the portals or cannulas used in the procedures. Similar elongated extensions are also used in open procedures. With respect to non-threaded or non-turnable suture anchors, these extensions merely are required to transmit longitudinal forces from the proximal end to the distal end where the suture anchor is situated. With respect to turnable or threaded suture anchors, the inserting device must be elongated as well as strong enough to transmit sufficient torque from the proximal end to the distal tip to turn the anchor.

Suture anchors are often shipped to the customers with the suture already joined to the anchor body and with the body in turn attached to the driver, i.e. pre-loaded. The driver must, therefore, accommodate suture while it is turning. For example, U.S. Pat. No. 5,411,506 (Goble et al.) and U.S. Pat. No. 5,411,523 (Goble) disclose a prior art suture anchor/driver assembly showing an anchor body preattached to sutures and held at the distal end of a cannulated driver. During arthroscopic or endoscopic procedures an elongated anchor/driver assembly enables a surgeon to manipulate the anchor within a portion of the body accessible only through a portal or other opening in the body. The suture anchor is provided with some means by which it may be attached and held to the distal end of the elongated driver while the proximal end is driven by the user.

It is also known to provide a user with an unthreaded suture anchor body which must then be threaded and attached to a driver. For example, U.S. Pat. No. 5,423,860 (Lizardi et al.) shows a device which facilitates loading a suture anchor into a non-cannulated driver. This device is a protective carrier in the form of a sleeve body which almost completely surrounds a suture anchor body having an aperture through its tip. The suture attached to the suture anchor is not retained by the protective carrier. The purpose of the protective carrier is to facilitate holding of the anchor as it is manipulated in order to thread a suture onto the anchor prior to assembling the anchor to the driver.

Suture anchor drivers may be either disposable or reusable. A significant factor in determining whether a particular driver is reusable is the ease with which a suture anchor may be threaded with suture and then threaded through or attached to the driver to produce a pre-loaded anchor/driver assembly. The small sizes of the eyelets or other apertures make threading suture a time consuming process at best, especially in an operating room setting. Additionally, such threading through either an eyelet of the anchor or through the axial bore of a driver requires the use of elongated needle threaders and thereby adds to the complexity of equipment required for given surgical procedures. The aforementioned Lizardi et al. patent shows one type of reusable driver system utilizing a non-cannulated driver. The drivers in the aforementioned Goble patents are, however, cannulated and, therefore, not amenable to being easily loaded by a user.

Prior art suture anchors are supplied to the customers pre-loaded as suture anchor/driver assemblies which utilize disposable cannulated drivers primarily because it is very difficult for a user to reuse the driver by attaching a suture to a new anchor body and then attaching the threaded anchor body to the driver. Attachment to a cannulated driver requires threading a flexible suture through a long, axial bore of the driver.

A co-pending patent application Ser. No. 08/597,792, assigned to the assignee hereof and incorporated by reference herein, discloses a pre-loaded suture anchor assembly and method of producing same which facilitates the attachment of a suture anchor to a driver. In one embodiment, the device utilizes a shrinkable tube encasing the ends of a length of suture (which is attached to a suture anchor) and provides some rigidity to facilitate threading the tube and suture through a cannulated driver. The tube is pulled through the driver until the anchor is seated at the distal end of the driver. In another embodiment, the device utilizes a short rod attached to the suture ends. The rod is "threaded" through the driver by simply being dropped through its bore under the influence of gravity. These devices are improved by the subject invention which facilitates not only the production of a pre-loaded suture anchor assembly but also facilitates threading it through a cannulated driver.

It is accordingly an object of this invention to provide a method and device for facilitating the attachment of a suture anchor to a driver.

It is also an object of this invention to provide a method and device for utilizing a pre-loaded suture anchor which may be easily assembled with a cannulated driver without use of other tools.

It is an additional object of this invention to provide a method and device for enabling a user (such as a surgeon or other health care worker) to easily load (i.e. thread) a pre-loaded suture anchor into a reusable cannulated driver.

SUMMARY OF THE INVENTION

These and other objects of the invention are achieved by the preferred embodiment disclosed herein which is a pre-loaded suture anchor assembly comprising an anchor body having a suture receiving means for receiving suture. The suture has a predetermined length and is threaded through the suture receiving means so as to have two ends extending therefrom. An elongated rod, having a proximal end and a distal end is placed in alignment with the suture ends and an elongated, tubular connecting member is used to engage the proximal end of the elongated rod and at least one of the first or second ends.

The invention also resides in a method of producing a pre-loaded suture anchor assembly for attachment to a suture anchor driver. The method comprises the steps of providing a suture anchor having a suture receiving means for receiving suture, providing a predetermined length of suture and engaging the suture with the suture receiving means so that at least one end of the suture extends from the suture anchor. The method further comprises providing an elongated rod, having a proximal end and a distal end, and providing an elongated tubular connecting member having an axial bore with open distal and proximal ends. One end of the suture is placed into one end of the connecting member and one end of the rod is placed into the other end of the connecting member. The connecting member is secured to the suture and rod ends, thus forming a pre-loaded suture anchor assembly.

BRIEF DESCRIPTION OF THE DRAWINGS

FIG. 1 is a side elevational view of a prior art suture anchor.

FIG. 2 is a left side view of FIG. 1.

FIG. 3 is a top plan view of FIG. 1.

FIGS. 4a and 4b are sequential views of the steps involved in forming one embodiment of the invention.

DESCRIPTION OF THE PREFERRED EMBODIMENT

Figure 5:
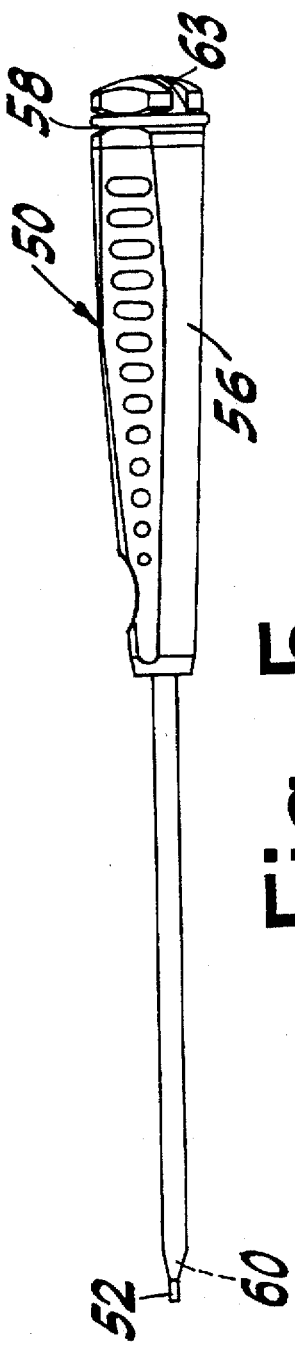
FIG. 5 is a side elevational view of a cannulated driver used to insert a suture anchor at a surgical site.

The method and apparatus of the present invention are best understood by reference to the FIGS. 4–7. While the invention is suitable for use with a variety of suture anchors, the preferred embodiment of the invention disclosed herein is explained in the context of a prior art threaded suture anchor 10 shown in FIGS. 1 through 3 and sold under the trademark REVO by Linvatec Corporation, 11311 Concept Boulevard, Largo, Fla. 33773. Suture anchor 10 comprises an anchor body 12 having a threaded distal portion 14, an apertured, proximal suture receiving portion 16 and an intermediate, hexagonally profiled drive portion 18. Suture receiving portion 16 has an eyelet 20 with an axis transverse to axis 22 of anchor body 12, the eyelet having a diameter sufficient to accommodate a selected suture.

As shown in FIG. 4a, eyelet 20 of suture anchor 10 is threaded (by means not shown) with a predetermined length of suture 30 which is long enough to be suitable for the procedure for which the suture anchor is intended. Suture 30 is threaded through the eyelet and folded back upon itself to have both ends placed side by side and to produce two equal-length suture portions extending from eyelet 20. (It is noted that some anchors and situations may utilize only a single suture portion extending from the anchor.) Both ends 30a and 30b are inserted (by means not shown) into a connecting member such as tube 32 which is adapted to engage the suture ends as will be understood below. An elongated rod 36, having a diameter approximately equal to that of both suture ends combined, has one of its ends 38 inserted into the other end of tube 32. While a fixed diameter tube 32 may be used by crimping, gluing or otherwise securing the suture and rod ends in the tube, tube 32 is preferably a material which initially has a large internal diameter, to easily receive the suture and rod ends and which can be then reduced in diameter. If shrink tubing is used, applying heat or some other stimulus to tube 32 (by means not shown) causes it to shrink around suture ends 30a, 30b and rod end 38 to a smaller diameter and frictionally engage both the suture and the rod end as shown in FIG. 4b. A short gap 39 may exist in the middled of the shrunken tube between the suture and rod ends. The length L of tube 32 need only be long enough to adequately grip the suture and rod ends. Thus, depending upon the initial tube diameter and length, the ends may be inserted easily in the tube from opposite sides without the aid of other tools. In the preferred embodiment, L is approximately 2 inches while rod 36 is approximately 10.5 and the suture is approximately 36 inches. The components shown in FIG. 4b comprise the anchor/suture/tubing/rod assembly, which will be simply referred to as the anchor assembly.

Figure 6:
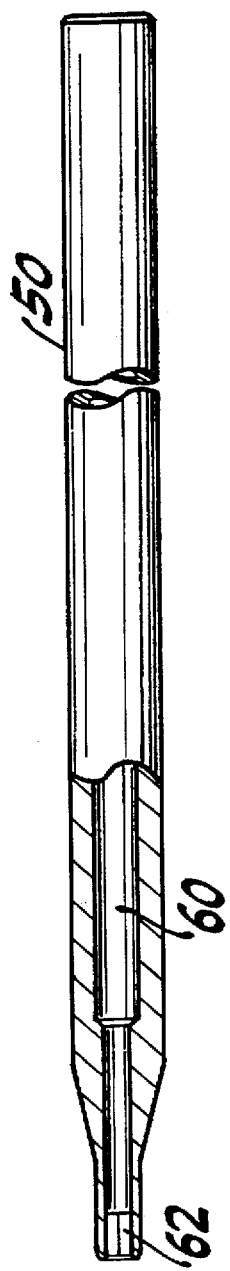
FIG. 6 is an exploded view of the distal tip of the driver of FIG. 5, partially in cross-section.

As shown in FIGS. 5 and 6, reusable suture anchor driver 50 has a distal tip 52, an elongated body 54, a handle 56, a suture retaining O-ring 58 and is cannulated throughout by axial bore 60 (best seen in FIG. 6). The distal end of bore 60 communicates with interior channel 62 in the hollow, hexagonal driver tip adapted to receive suture and drive portion 18 of the suture anchor. Driver 50 is known and often used with a threaded suture anchor such as anchor 10. However, prior to this invention, such use required the user to laboriously thread suture through the anchor body and then through the bore 60 of the driver. After this was done and the anchor was seated at the distal tip of the driver, the suture extending from the proximal, handle end of bore 60 was held in place by lying in one of three radially extending grooves 63 (between bore 60 and O-ring 58) and being wrapped circumferentially around the driver handle adjacent O-ring 58. As will be understood below, the invention facilitates the assembly of the anchor with the driver. Rod 36 and tube 32, after shrinking, must be sufficiently small in diameter to enable it to pass through channel 62 and bore 60.

In one preferred embodiment of this invention the maximum dimension of suture retaining portion 16 is 0.064 inches while the maximum dimension of the hexagonal drive portion 18 across the flats is 0.077 inches. It has been found that shrinkable tubing having an outside diameter of 0.072 inches before heating and an outside diameter of 0.065 inches after heating is suitable for use with such an anchor. While numerous types of heat skrinkable tubing may be used, the shrink tubing may be, for example, fluorinated ethylenepropylene having a minimum expanded ID of 0.060 and a maximum recovered ID of 0.049. With respect to a second example, a smaller, Mini-REVO suture anchor having a maximum eyelet dimension of 0.055 inches and a maximum hexagonal dimension across the flats of 0.0557 may also be used. For this embodiment a shrinkable tube having an outside dimension of 0.062 inches before heating and 0.054 inches after heating is suitable, this shrink tubing having a minimum expanded ID of 0.054 inches and a maximum recovered ID of 0.044 inches. Both REVO and Mini-REVO suture anchors are usable with number 0 braided polyester suture (3.55 mm metric) having an outside diameter of 0.35 mm min/0.399 mm max and, since the shrinkage of the tubing is effective over a wide range, the system is also usable with a number 1 or 2 braided polyester suture (4mm, 5mm) having an outside diameter of 0.40 mm min/0.499 mm max or 0.50 mm min/0.599 mm max, respectively.

Figure 7:
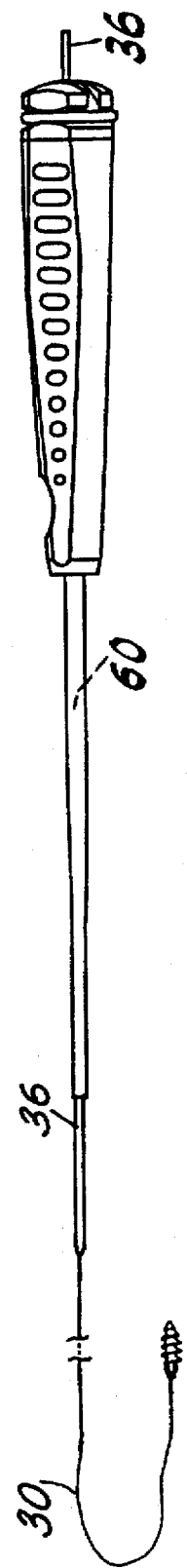
FIG. 7 shows the manner in which the embodiment of the invention shown in FIG. 4b may be loaded into a cannulated driver.

As shown in FIG. 7, the embodiment of FIG. 4b is used by holding the driver in any orientation and simply pushing the free end of rod 36 into the distal tip and through bore 60 of the driver until it emerges from the proximal, handle end of the driver bore. The rod should be longer than the driver to facilitate loading. The free end of the anchor assembly may then be pulled the rest of the way until the anchor is eventually seated in channel 62. The tubing is then removed from the suture by either cutting it off or pulling it off once it is threaded through the driver.

It will be understood by those skilled in the art that numerous improvements and modifications may be made to the preferred embodiments of the invention disclosed herein without departing from the spirit and scope thereof.

What is claimed is:

1. A pre-loaded suture anchor assembly for attachment to an anchor driver comprising:

an anchor body having a suture receiving means for receiving suture;

a suture having predetermined length and having a first end and a second end, said suture received in said suture receiving means and extending therefrom;

an elongated, substantially straight rod, having a proximal end and a distal end; and an elongated, tubular connecting member for engaging the proximal end of said elongated rod and said first or second suture ends.

2. A pre-loaded suture anchor assembly according to claim 1 wherein said elongated, tubular connecting member is a hollow, elongated tubular sleeve having an axial bore with open distal and proximal ends for receiving and frictionally engaging said ends of said suture in the proximal end of said sleeve and said end of said rod in the distal end of said sleeve.

3. A pre-loaded suture anchor assembly according to claim 1 wherein said connecting member frictionally engages predetermined portions of the end of said elongated rod and said suture ends.

4. A pre-loaded suture anchor assembly according to claim 1 wherein said connecting member comprises a heat-shrinkable tube.

5. A method of producing a pre-loaded suture anchor assembly comprising a suture anchor for securing selected tissue thereto, said assembly for being received within and adjacent one end of a throughbore extending entirely through a cannulated suture anchor driver comprising the steps of:

providing a suture anchor having a suture receiving means for receiving suture;

providing a predetermined length of suture;

engaging said predetermined length of suture with said suture receiving means so that at least one end of said suture extends from said suture anchor to enable said suture to secure selected tissue thereto;

providing an elongated, substantially straight rod having a proximal end and a distal end;

providing an elongated tubular connecting member having an axial bore with open distal and proximal ends;

placing said at least one end of said suture into one end of said connecting member and said proximal end of said rod into the other end of said connecting member;

causing said tubular connecting member to engage said at least one end of said suture and said proximal end of said rod.

6. A method according to claim 5 wherein said tubular connecting means is shrinkable tubing and further comprising the step of:

activating said tubular connecting means in order to cause it to frictionally engage said suture.

7. A method according to claim 5 further comprising the steps of:

providing a cannulated anchor driver having an axial bore and an anchor engaging means at its distal end for engaging said anchor in order to enable it to be driven at a predetermined work site;

placing said distal end of said elongated rod into the distal end of said axial bore and through the axial bore of said cannulated anchor driver;

pulling the assembly through the axial bore until the anchor is seated at the distal tip of the driver.

8. A method of enabling a user to load a pre-loaded suture anchor assembly into an elongated cannulated driver for driving a suture anchor comprising the steps of:

providing a pre-loaded suture anchor assembly comprising a suture anchor, a predetermined length of suture having a predetermined proximal portion thereof contiguous to said suture anchor and at least one distal unattached end portion, an elongated rod and an elongated connecting member for securing one end of said rod in an endwise manner to said at least one distal end portion of said suture;

providing a cannulated driver having an axially aligned throughbore entirely therethrough;

axially inserting said elongated rod into and through said throughbore of said cannulated driver sufficiently to pass said elongated rod entirely through said throughbore to enable it to be grasped by the user;

seating said suture anchor in the driver to enable it to be driven thereby; and removing said connecting member and rod from said assembly.

* * * * *